United States Patent
Grandeury et al.

(10) Patent No.: US 8,987,448 B2
(45) Date of Patent: Mar. 24, 2015

(54) PREPARATION OF ANHYDROUS AND HYDRATED POLYMORPHS 4-AMINO-5-FLUORO-3-[6-(4-METHYLPIPERAZIN-1-YL)-1H-BENZIMIDAZOL-2-YL]-1H-QUINOLIN-2-ONE-LACTIC ACID SALT

(75) Inventors: Arnaud Grandeury, Helfrantzkirch (FR); Christian Riegert, Sierentz (FR); Andreas Schreiner, Rheinfelden (CH)

(73) Assignee: Novartis AG, Basel (CH)

( * ) Notice: Subject to any disclaimer, the term of this patent is extended or adjusted under 35 U.S.C. 154(b) by 155 days.

(21) Appl. No.: 13/637,048

(22) PCT Filed: Mar. 25, 2011

(86) PCT No.: PCT/EP2011/054607
§ 371 (c)(1),
(2), (4) Date: Sep. 25, 2012

(87) PCT Pub. No.: WO2011/117380
PCT Pub. Date: Sep. 29, 2011

(65) Prior Publication Data
US 2013/0018188 A1 Jan. 17, 2013

Related U.S. Application Data

(60) Provisional application No. 61/317,943, filed on Mar. 26, 2010.

(51) Int. Cl.
*C07D 401/04* (2006.01)
(52) U.S. Cl.
CPC .................................. *C07D 401/04* (2013.01)
USPC .......................................................... 544/363
(58) Field of Classification Search
None
See application file for complete search history.

(56) References Cited

U.S. PATENT DOCUMENTS 7,838,527 B2 * 11/2010 Hannah et al. ............ 514/255.02
8,614,216 B2 * 12/2013 Okhamafe et al. ........ 514/253.07

FOREIGN PATENT DOCUMENTS

WO  WO 2005/046590    5/2005
WO  WO 2006/127926   11/2006

OTHER PUBLICATIONS

Qu H et al. "Solubility and stability of anhydrate/hydrate in solvent mixtures", International Journal of Pharmaceutics, vol. 321, No. 1-2, pp. 101-107, 2006.
Zhu et al., "Influence of water activity in organic solvent + water mixtures on the nature of the crystalizing drug phase. 1. Theophylline" International Journal of Pharmaceutics, vol. 135, pp. 151-160, 1996.
Zhu, Haijian et al: "influence of water activity in organic solvent + water mixtures on the nature of the crystallizing drug phase. 1. Theophylline", International Journal of Pharmaceutics, vol. 135, pp. 151-160, 1996.
Handbook for preparing crystal of organic compound-principles and know-how-Maruzen Co., Ltd., Jul. 25, 2008, pp. 57-84 (Translation of relevant parts).

* cited by examiner

*Primary Examiner* — Sun Jae Yoo
(74) *Attorney, Agent, or Firm* — Gregory Ferraro

(57) ABSTRACT

The present technology provides methods of making anhydrous crystalline Form II and monohydrate crystalline Form B of the lactic acid salt of 4-amino-5-fluoro-3-[6-(4-methylpiperazin-1-yl)-1H-benzimidazol-2-yl]-1H-quinolin-2-one.

14 Claims, 1 Drawing Sheet

PREPARATION OF ANHYDROUS AND HYDRATED POLYMORPHS 4-AMINO-5-FLUORO-3-[6-(4-METHYLPIPERAZIN-1-YL)-1H-BENZIMIDAZOL-2-YL]-1H-QUINOLIN-2-ONE-LACTIC ACID SALT

This application is a 371 of PCT/EP2011/054607 filed on Mar. 25, 2011, which claims benefit of U.S. Provisional Application No. 61/317,943, filed Mar. 26, 2010, which in its entirely is herein incorporated by reference.

FIELD

The present technology relates to a methods of preparing anhydrous and hydrated polymorphs of 4-amino-5-fluoro-3-[6-(4-methylpiperazin-1-yl)-1H-benzimidazol-2-yl]-1H-quinolin-2-one lactic acid salt.

BACKGROUND

The following description is provided to assist the understanding of the reader. None of the information provided or references cited herein are admitted to be prior art to the present technology.

4-Amino-5-fluoro-3-[6-(4-methylpiperazin-1-yl)-1H-benzimidazol-2-yl]-1H-quinolin-2-one has the structure shown in Formula I:

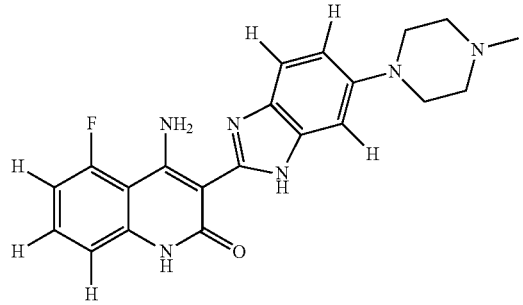

I

The compound of Formula I inhibits various protein kinases, such as tyrosine receptor protein kinase inhibitors. Consequently, the compound of Formula I and its salts are useful for inhibiting angiogenesis and treating cancers such as multiple myeloma (MM), acute myelogenous leukemia (AML), prostate cancer, breast cancer, renal cancer, colon cancer, and melanoma. Use and preparation of this compound and its salts, including the mono-lactic acid salt, are described in U.S. Pat. Nos. 6,605,617, 6,774,237, 7,335,774, and 7,470,709, and in U.S. patent application Ser. Nos. 10/982,757, 10/982,543, and 10/706,328, and in the published PCT applications WO2006/127926, published on Nov. 30, 2006 and WO2009/115562 published on Sep. 24, 2009, each of which is incorporated herein by reference in its entirety.

The monolactate salt of the compound of Formula I exists in a variety of polymorphs, including, e.g., the monohydrate Form B and the anhydrous Form II. Polymorphs occur where the same composition of matter (including its hydrates and solvates) crystallizes in a different lattice arrangement resulting in different thermodynamic and physical properties specific to the particular crystalline form. Because physical properties of polymorphs can vary markedly and may affect the biological properties of a drug (e.g., bioavailability), it is important to be able to reliably produce a drug such as the compound of Formula I with little or no contamination by other polymorphs. The aim of the present invention is to provide such a process of preparing a polymorphic form of the lactic acid salt of 4-amino-5-fluoro-3-[6-(4-methylpiperazin-1-yl)-1H-benzimidazol-2-yl]-1H-quinolin-2-one.

SUMMARY

The present technology is directed to methods of preparing anhydrous and hydrated polymorphs of the lactic acid salt of 4-amino-5-fluoro-3-[6-(4-methylpiperazin-1-yl)-1H-benzimidazol-2-yl]-1H-quinolin-2-one. Thus, in one aspect there are provided methods of making Form B, a monohydrate crystalline form of a lactic acid salt of a compound of Formula I,

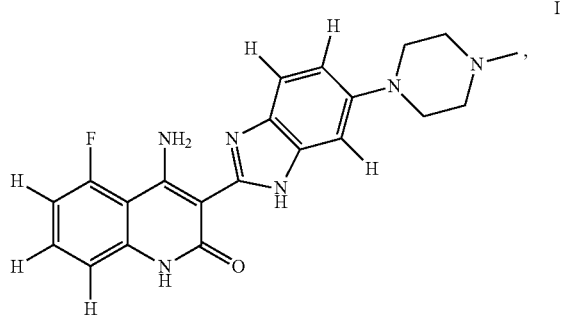 [SMILES: CN1CCN(c2ccc3nc(-c4c(N)c5c(F)cccc5[nH]c4=O)[nH]c3c2)CC1]

I comprising: heating a suspension of the free base of the compound of formula I and lactic acid or of a polymorph of a lactic acid salt of compound of Formula I, or of a mixture of polymorphs of a lactic acid salt of compound of Formula I, in a solution comprising at least 2 solvents, said solution having a water activity of about 0.3 to about 0.6 for example a solution of about 8 weight percent (wt %) to about 16 wt % water in ethanol, for example 9 wt % to about 15 wt %, e.g. 10 wt % to about 15 wt %, e.g. 10 wt % to about 14 wt %, e.g. 10 wt % to about 13 wt %, or e.g. 12 wt % to about 14 wt %, or e.g. 11 wt % to about 15 wt %, e.g. 12 wt % to about 15 wt %, e.g. 13 wt % water in ethanol at a temperature of, for example, about 20° C. to 70° C., e.g. at least about, 60° C., e.g. 55° C., e.g. 68° C., e.g. at e.g. 50° C., or e.g. about 30° C. to 70° C., e.g. about 40° C. to 70° C., e.g. about 50° C. to 70° C., e.g. about 55° C. to 65° C.; and isolating crystals of substantially pure form B from the solution at a temperature of, e.g. about 20° C. to 70° C., e.g. at least about 50° C., or e.g. 50° C. to 70° C., or at 55° C. or at 60° C. or at 65° C.

Within the scope of the present invention, it has to be understood that the different steps of the process although described individually can be combined together.

The formation of anhydrous and/or hydrated forms depends strongly on the water activity present at the formation of the salt. The water activity is defined as the product of the water activity coefficient and the mole fraction of water in the aqueous fraction. The role of the water activity in solid-state stability is well recognized for example in Zhu, H. and Grant, D. J.; Int. I. Pharm., 1996, 139, 33-43. It is also recognized through the solvate rule that at higher water activity hydrates are more stable than the anhydrous form, see for example Variankaval N. et al., Organic Process Research and Development 2007, 11, 229-236.

According to the present invention, the process comprises: heating a suspension of the free base of the compound of formula I and lactic acid in a solution, for example, e.g. with a water activity of about 0.3 to about 0.6, which can e.g. be adjusted by, e.g. about 8 weight percent (wt %) to about 16 wt % water in ethanol, at a temperature of at least about 20° C. to about 70° C., e.g. 30° C. to 70° C., e.g. about 40 to 70° C., e.g. about 50 to 70° C., e.g. 50° C.; and isolating crystals of substantially pure form B from the solution at a temperature of about 20° C. to 70° C., e.g. of about at least about 50° C.

Within the present invention, the term 'solution' means a mixture of at least two solvents, for example a mixture of water and ethanol.

A solution used in the process according to the present invention comprises at least two solvents, one of which can for example be water. The solution cannot consist of only water as a solvent. The person skilled in the art would recognised further embodiments of the present invention such as combining different appropriate solvents to form the solution to achieve a water activity according to the one of the present invention, said solution is used to prepare the suspension.

The term 'suspension' according to the present invention refers to the material, e.g. the free base of the compound of formula I and lactic acid or a polymorphic form or a mixture of polymorphs of the lactic acid salt of compound of formula I, being mixed in the solution as defined above to form the suspension.

For water activities below 0.3 or above 0.6, the formation of the form B might be feasible, however the process cannot be regarded as robust as mixtures of hydrated and anhydrated forms could appear.

The impact of the lactic acid or impurities may alter the value of the water activity and is not considered in the water activity range.

In some embodiments of the methods of making Form B, the lactic acid is D,L lactic acid. In other embodiments, the lactic acid is depolymerized lactic acid. In some embodiments, the suspension comprises about 1 to about 3 molar equivalents of lactic acid per molar equivalent of the compound of formula I.

In some embodiments of the methods of making Form B, the solution contains about 12 wt % to about 14 wt % water in ethanol, as an example to adjust the water activity conditions within the range of 0.3 to 0.6.

In some embodiments of the methods of making Form B, the suspension is heated to a temperature ranging from about 20° C. to about 70° C., or from about 55° C. to about 65° C., e.g. the suspension is heated to a temperature of at least about 60° C.

The methods of making Form B may further include drying the isolated crystals of Form B, e.g., under reduced pressure. In some embodiments, the crystals are dried at a temperature in the range of about 30° C. to about 60° C.

In some embodiments of the methods of making Form B, the suspension comprises about 1.5 to about 2.5 molar equivalents of depolymerized D,L-lactic acid per molar equivalent of the compound of formula I; the solution has a water activity of about 0.3 to about 0.6, e.g. the solution contains about 12 wt % to about 14 wt % water in ethanol; the suspension is heated to a temperature ranging from at least about 60° C. to about 70° C.; and the crystals of substantially pure Form B are isolated from the solution at a temperature of at least about 60° C.

In the methods of making Form B according to the present invention, the isolated crystals may comprise at least 95 wt % Form B.

In another aspect, the present technology provides methods of making Form II, an anhydrous crystalline form of a lactic acid salt of the compound of Formula I. The methods include heating a suspension of a lactate salt of the compound of Formula I, other than Form II, and lactic acid in a $C_{1-4}$ alcohol without added water at a temperature of at least about 40° C., and isolating crystals of substantially pure Form II from the solution at a temperature of at least about 30° C. In other embodiments the crystals of substantially pure Form II are isolated from the solution at a temperature of at least about 40° C. or at least about 50° C. In some embodiments, the lactate salt of the compound of Formula I is anhydrous Form A or monohydrate Form B.

In some embodiments of the methods of making Form II, the lactic acid is D,L-lactic acid. In some embodiments, the amount of lactic acid ranges from about 1 to about 1.2 molar equivalents of the compound of Formula I.

In one embodiment to prepare Forms B, the water activity can be adjusted with the $C_{1-4}$ alcohols, e.g. methanol, ethanol, n-propanol, isopropanol, n-butanol, sec-butanol, isobutanol, tert-butanol, or a mixture of any two or more thereof. In an illustrative embodiment, the alcohol is absolute ethanol.

In one embodiment to prepare Form II, the suspension is heated to a temperature in the range from about 40° C. to about 120° C. In another embodiment, the suspension is heated to a temperature in the range from about 40° C. to about 70° C.

The methods of making Form B may further include drying the isolated crystals of Form II, e.g., under reduced pressure. In some embodiments, the crystals are dried at a temperature in the range of about 30° C. to about 60° C.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
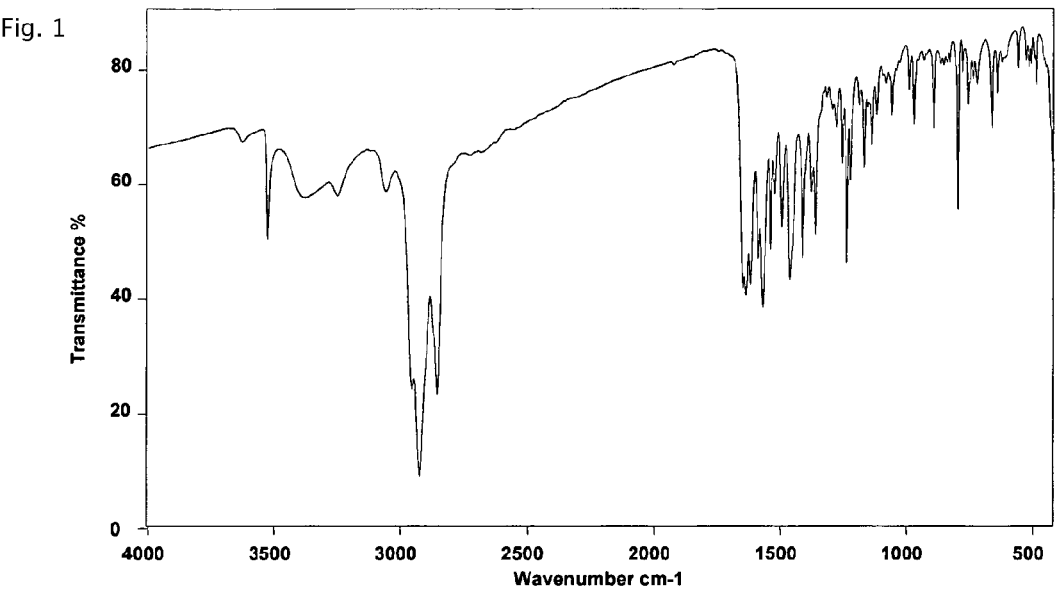
FIG. 1 shows an illustrative embodiment of the FTIR spectrum of the Form B polymorph of 4-amino-5-fluoro-3-[6-(4-methylpiperazin-1-yl)-1H-benzimidazol-2-yl]-1H-quinolin-2-one lactic acid salt monohydrate.

The present technology provides methods of making Form B, a monohydrate crystalline form of the lactic acid salt of a compound of Formula I, and Form II, the anhydrous crystalline form of the lactic acid salt of a compound of Formula I. The present methods reliably produce substantially pure Form B and Form II polymorphs. One advantage of the present invention is that pure or substantially pure Form B can be prepared starting from any polymorphic form or mixture of polymorphs of 4-amino-5-fluoro-3-[6-(4-methylpiperazin-1-yl)-1H-benzimidazol-2-yl]-1H-quinolin-2-one lactic acid salt.

The present methods of making Form B, a monohydrate crystalline form of a lactic acid salt of a compound of Formula I, include heating a suspension of the free base of the compound of Formula I and lactic acid in a solution of water in ethanol. The free base of the compound of Formula I may be prepared by known methods as described in, e.g., WO 2006/127926 (Example 1, steps A-C). The compound of Formula I does not completely dissolve in the ethanol/water solution but exists as a slurry in the present methods. Thus, the volume of aqueous ethanol must be large enough to allow for the suspension of the compound during heating. While the exact amount of solvent is not critical, larger amounts such as 2-10 ml per mmol of compound conveniently allow for suspension of the compound using typical stirring configurations (e.g., paddle, anchor, etc.). Smaller or larger amounts of solvent may be used so long as the compound is kept in suspension.

Commercial grade D,L-lactic acid may be used in the present methods. Commercial grade lactic acid contains dimers, trimers and higher polymers of lactic acid. Form B is a monolactate salt; the compound of Formula I does not crystallize out as a salt with the dimer or higher polymers of the lactic acid. Thus, although not required, the lactic acid may be depolymerized to increase the percentage of monomeric lactic acid present in the reagent. Depolymerization may be effected by any suitable method such as by heating the lactic acid in water to 100° C. for 20-24 hours or longer as necessary.

At least one molar equivalent of lactic acid per molar equivalent of the free base of the compound of Formula I is typically used in the present methods. However, a molar excess of lactic acid may be advantageously used. Thus, in some embodiments, the amount of lactic acid ranges form about 1 molar equivalent to about 3 molar equivalents, or from about 1.5 to about 2.5 molar equivalents or about 2 molar equivalents per molar equivalent of the compound of Formula I. While not wishing to be bound by theory, the excess lactic acid is believed to stabilize the pH of the reaction system and drive the reaction forward.

Surprisingly, it has been discovered that controlling the amount of water present in the reaction (as well as the temperature) is important to reliably obtain Form B in a substantially pure form and in good yield. Thus, in order to avoid producing anhydrous polymorphs or the dihydrate or higher hydrates of the lactic acid salt of the compound of Formula I, only a relatively narrow range of water, e.g. water activity may be used, e.g. about 8 wt % to about 16 wt % water in ethanol (based on the total weight of water and ethanol). In some embodiments, the amount of water used, e.g. in the solution, e.g. with ethanol, ranges from about 9 wt % to about 15 wt %, from about 10 wt % to about 15 wt %, from about 10 wt % to about 14 wt %, from about 10 wt % to about 13 wt %, from about 11 wt % to about 15 wt %, from about 12 wt % to about 15 wt %, from about 12 wt % to about 14 wt %, or is about 13 wt %.

In order to accurately control the amount of water present in the reaction, the amount of adventitious water present in the reaction reagents and solvent must be taken into account before the amount of added water can be determined. For example, the amount of water in the ethanol used must be known. To simplify matters, water-free ethanol such as absolute ethanol may be used. Denatured ethanol (e.g., containing toluene as a denaturant) may also be used so long as the water content is known and accounted for. Likewise, the lactic acid used in the reaction can be a major source of water. Commercial grade lactic acid may contain, e.g., about 15 wt % water. Depolymerized lactic acid may contain as much as 65-67 wt % water. Hence, when using depolymerized lactic acid, significantly less water must be added to the ethanol to reach the correct percentage for the reaction.

The table below provides examples of correlation between water activity in water/ethanol mixtures for 60° C., this correlation was performed using a computer calculation, known by the person skilled in the art, and conducted using the software aspen batch plus in the present case.

| Temp. in ° C. | Molecular Fraction | | Mass fraction of water in solution | Water activity |
|---|---|---|---|---|
| | Ethanol | Water | | |
| 60 | 0 | 1 | 1 | 1 |
| 60 | 0.025 | 0.975 | 0.938477581 | 0.976629225 |
| 60 | 0.05 | 0.95 | 0.881397866 | 0.9561579 |
| 60 | 0.075 | 0.925 | 0.828296396 | 0.938106325 |
| 60 | 0.1 | 0.9 | 0.778771272 | 0.9220635 |
| 60 | 0.125 | 0.875 | 0.732472968 | 0.90767425 |
| 60 | 0.15 | 0.85 | 0.689096068 | 0.89462415 |
| 60 | 0.175 | 0.825 | 0.648372519 | 0.8826378 |
| 60 | 0.2 | 0.8 | 0.61006609 | 0.8714648 |
| 60 | 0.225 | 0.775 | 0.573967784 | 0.860881625 |
| 60 | 0.25 | 0.75 | 0.539892022 | 0.850683 |
| 60 | 0.275 | 0.725 | 0.507673455 | 0.8406781 |
| 60 | 0.3 | 0.7 | 0.477164281 | 0.8306907 |
| 60 | 0.325 | 0.675 | 0.448231974 | 0.8205543 |
| 60 | 0.35 | 0.65 | 0.420757363 | 0.8101106 |
| 60 | 0.375 | 0.625 | 0.394632991 | 0.79921 |
| 60 | 0.4 | 0.6 | 0.369761709 | 0.7877076 |
| 60 | 0.425 | 0.575 | 0.346055469 | 0.7754634 |
| 60 | 0.45 | 0.55 | 0.323434284 | 0.7623418 |
| 60 | 0.475 | 0.525 | 0.301825325 | 0.74821005 |
| 60 | 0.5 | 0.5 | 0.281162137 | 0.7329385 |
| 60 | 0.525 | 0.475 | 0.261383959 | 0.7163988 |
| 60 | 0.55 | 0.45 | 0.242435126 | 0.69846525 |
| 60 | 0.575 | 0.425 | 0.224264544 | 0.679013575 |
| 60 | 0.6 | 0.4 | 0.206825233 | 0.6579204 |
| 60 | 0.625 | 0.375 | 0.190073918 | 0.63506325 |
| 60 | 0.65 | 0.35 | 0.173970674 | 0.61032125 |
| 60 | 0.675 | 0.325 | 0.158478605 | 0.5835739 |
| 60 | 0.7 | 0.3 | 0.143563567 | 0.5547015 |
| 60 | 0.725 | 0.275 | 0.129193908 | 0.523585425 |
| 60 | 0.75 | 0.25 | 0.115340254 | 0.490107 |
| 60 | 0.775 | 0.225 | 0.101975299 | 0.454149225 |
| 60 | 0.8 | 0.2 | 0.089073634 | 0.4155952 |
| 60 | 0.825 | 0.175 | 0.076611579 | 0.374329025 |
| 60 | 0.85 | 0.15 | 0.064567042 | 0.33023565 |
| 60 | 0.875 | 0.125 | 0.052919386 | 0.28320125 |
| 60 | 0.9 | 0.1 | 0.041649313 | 0.2331128 |
| 60 | 0.925 | 0.075 | 0.030738755 | 0.179858325 |
| 60 | 0.95 | 0.05 | 0.020170779 | 0.1233273 |
| 60 | 0.975 | 0.025 | 0.009929501 | 0.063410475 |
| 60 | 1 | 0 | 0 | 0 |

Unexpectedly, control over the temperature of the reaction in conjunction with the amount of water present also significantly affects the purity of Form B produced. For example, at reaction temperatures of 30° C. and below, such as at room temperature, mixtures of polymorphs or polymorphs other than Form B may be produced, even using the limited amounts of water described above. Hence, in the present methods, the suspension is advantageously heated at a temperature of about 20° C. to 70° C., e.g. at least about 50° C., at least about 55° C. or at least about 60° C. In some embodiments, the suspension is heated to a temperature ranging from about 50° C. to about 70° C., or about 55° C. to about 65° C., or about 68° C. To allow the lactate salt to equilibrate to Form B, the suspension is heated for a suitable period of time, e.g., about 4 to about 12 hours, about 6 to about 10 hours, or about 8 hours.

Surprisingly, the need for control over temperature extends to the isolation step in the present methods. Allowing the reaction solution to cool prior to filtration may lead to precipitation of undesired polymorphs. Thus, the methods of making Form B further include isolating crystals of substantially pure Form B from the solution at a temperature of at least about 50° C., at least about 55° C., at least about 60° C., or at least about 65° C. The crystals of Form B may be conveniently separated from the reaction mixture by standard methods of filtration. To minimize cooling of the mixture during filtration, the filter (e.g. filter pad, filter cloth, sintered funnel, or suction funnel with filter paper) may be preheated to the same or a similar temperature as the reaction mixture. Crystals of Form B may also be isolated by centrifugation of the hot reaction mixture.

Methods of making Form B may further include drying the isolated crystals of Form B. The drying may take place at atmospheric pressure or under reduced pressure (e.g., at a pressure ranging from about 20 mbar to about 200 mbar, from about 50 mbar to about 150 mbar, or at about 100 mbar). The crystals may be dried at room temperature or an elevated temperature such as a temperature in the range of about 30° C. to about 60° C., or from about 30° C. to about 50° C., or at about 40° C. Drying may be carried out for about 4 hours to about 24 hours, and typically for about 8 hours to about 12 hours.

It will be understood that the skilled artisan may combine or vary any of the conditions described above to optimize the methods for the particular application at hand. For example, in some embodiments of the present methods, the suspension comprises about 1.5 to about 2.5 molar equivalents of depolymerized D,L-lactic acid per molar equivalent of the compound of formula I; the solution contains about 12 wt % to about 14 wt % water in ethanol; the suspension is heated to a temperature ranging from at least about 60° C. to about 70° C.; and the crystals of substantially pure Form B are isolated from the solution at a temperature of at least about 60° C.

The present methods of preparing Form B can provide substantially pure Form B. By "substantially pure Form B" it is meant that the isolated crystals comprises at least 90 wt % Form B (i.e., 10 wt % or less of impurities, amorphous material or other crystalline forms of the compound of Formula I). In some embodiments of the present methods, the isolated crystals comprise at least 95 wt %, at least 96 wt %, at least 97 wt %, at least 98 wt %, or at least 99 wt % Form B. In some embodiments of the invention, pure Form B is obtained.

In another aspect, the present technology provides methods of making Form II, an anhydrous crystalline form of a lactic acid salt of a compound of formula I. The methods include heating a suspension of a lactate salt of the compound of Formula I and lactic acid in a $C_{1-4}$ alcohol without added water, at a temperature of at least about 30° C. Any monolactate salt of the compound of Formula I (other than Form II itself) may be used in the present methods, including but not limited to, anhydrous Form A (WO 2006/127926, Example 1) or monohydrate Form B. In the present methods, D,L-lactic acid, such as commercial grade D,L-lactic acid may be used. Also, the lactic acid may optionally be depolymerized.

Similar to the free base of the compound of Formula I in the methods of making Form B above, the lactic acid salt of the compound of Formula I does not completely dissolve in the $C_{1-4}$ alcohol but exists as a slurry. Thus, the volume of $C_{1-4}$ alcohol must be large enough to allow for the suspension of the salt during heating, but not so large as to mostly dissolve the salt. As above, the exact amount of solvent is not critical, and larger amounts such as 2-10 ml per mmol of compound conveniently allow for suspension of the compound using typical stirring configurations (e.g., paddle, anchor, etc.). Smaller or larger amounts of solvent may be used so long as the compound is kept in suspension.

A range of amounts of lactic acid may be used in the methods of making Form II. For example, the amount of lactic acid may range from about 1 to about 2, about 1 to about 1.5, or about 1 to about 1.2 molar equivalents of the compound of formula I. However, less than a molar equivalent of lactic acid per mole of the lactate salt of the compound of Formula I may also be used in the present methods. Thus, in one embodiment, the amount of added lactic acid ranges from about 0.05 to about 0.9 molar equivalents. In some embodiments, the amount of added lactic acid ranges from about 0.1 to about 0.5 molar equivalents or from about 0.1 to about 0.2 equivalents.

In the present methods of making Form II, the solvent is a $C_{1-4}$ alcohol, typically without added water. In some embodiments, the $C_{1-4}$ alcohol is selected from methanol, ethanol, n-propanol, isopropanol, n-butanol, sec-butanol, isobutanol, and tert-butanol. In an illustrative embodiment, the alcohol is absolute ethanol. While no water is preferably added to the reaction, the skilled artisan will understand that the present methods may employ solvents containing small amounts of adventitious water. In some embodiments, the total water content of the reaction mixture is less than about 5%. In other embodiments, the total water content of the reaction mixture is less than about 4%, less than about 3%, less than about 2%, or less than about 1%.

In the present methods, the suspension of the lactate salt of the compound of Formula I and lactic acid in a $C_{1-4}$ alcohol is heated to at least about 40° C., at least about 50° C., or at least about 60° C. In some embodiments, the suspension is heated to a temperature in the range from about 40° C. to about 120° C. Alternatively, the suspension may be heated to a temperature in the range from about 40° C. to about 70° C. or from about 50° C. to about 70° C.

To obtain the anhydrous crystalline Form II of the lactate salt of the compound of Formula I, the suspension is heated for a suitable time. For example, the suspension may be heated for a period of time from about 1 to about 100 h. In some embodiments, the suspension is heated for a period of time from about 10 to about 40 h, or from about 15 to about 25 h. To form the suspension, the reaction mixture may be stirred. The stirring speed can be adjusted to ensure effective mixing of the reactants. Thus, in one embodiment, the suspension is stirred at a speed of about 100 to about 500 rpm. In some embodiments, the suspension is stirred at a speed of about 100 to about 300 rpm, and in another embodiment, at about 200 rpm.

The present methods of making Form II further include isolating crystals of substantially pure Form II from the solution at a temperature of at least about 30° C. Warmer temperatures for the isolation may also be used such as at least about 40° C., at least about 50° C., at least about 55° C., at least about 60° C., or at least about 65° C. Isolating the crystals from the warm reaction mixture can help avoid the formation of undesired polymorphs, especially if the reaction solvent contains some water. The crystals of Form II may be isolated from the suspension by any suitable method known in the art, such as, e.g., using filtration through a suitable filter medium or by centrifugation. To minimize cooling of the mixture during filtration, the filter (e.g., filter pad, filter cloth, sintered funnel, or suction funnel with filter paper) may be preheated to the same or a similar temperature as the reaction mixture.

Methods of making Form II may further include drying the isolated crystals of Form II. The drying may take place at atmospheric pressure or under reduced pressure (e.g., at a pressure ranging from about 20 mbar to about 200 mbar, from about 50 mbar to about 150 mbar, or at about 100 mbar). The crystals may be dried at room temperature or an elevated temperature such as a temperature in the range of about 30° C. to about 60° C., or from about 30° C. to about 50° C., or at about 40° C. Drying may be carried out for any suitable time period such as about 1 to about 24 hours, or from about 4 hours to about 24 hours, and typically for about 8 hours to about 12 hours.

The methods for preparation of Form II provided herein can result in substantially pure Form II. By "substantially pure Form II" it is meant that the isolated crystals comprises at least 90 wt % Form II (i.e., 10 wt % or less of impurities, amorphous material or other crystalline forms of the compound of Formula I). In some embodiments of the present methods, the isolated crystals comprise at least 95 wt %, at least 96 wt %, at least 97 wt %, at least 98 wt %, or at least 99 wt % Form II. In some embodiments, the remainder lactic acid salt of the compound of Formula I is present in amorphous form or one or more other crystalline forms (including solvates and hydrates) such as Form A, B, C, D, E, F, G, H, and/or I. Amounts of different crystalline forms of in a composition can be determined by routine spectroscopic methods, such as X-ray powder diffraction, DSC, and the like.

The present technology can be further illustrated by the following non-limiting examples.

EXAMPLES

Example 1

Preparation of the Crystalline Monohydrate Form of 4-amino-5-fluoro-3-[6-(4-methylpiperazin-1-yl)-1H-benzimidazol-2-yl]-1H-quinolin-2-One Lactic Acid Salt (Form B)

A 500 ml double jacket reactor with a condenser, temperature probe, nitrogen inlet, and mechanical stirrer was purged with nitrogen. The reactor was charged with 15.0 g 4-amino-5-fluoro-3-[6-(4-methylpiperazin-1-yl)-1H-benzimidazol-2-yl]-1H-quinolin-2-one as the free base, which may be prepared as described in WO 2006/127926, see Example 1, steps A-C, pp. 63-71, 20.0 g depolymerized D,L-lactic acid (containing 37% lactic acid, of which 92% was monomer, and 63% water; prepared from 85 wt % D,L-lactic acid that was stirred in 100° C. water for 20-24 h), 160 g water-free ethanol, and 12 g water. The mixture was stirred vigorously (100 rpm) to form a brownish suspension and heated to an external temperature of 60° C. over 1 h (internal temperature of 58° C.). Seed crystals of Form B (0.12 g) were added to the suspension immediately upon reaching 60° C. The suspension was stirred at this temperature for 8 h. The water activity in the present example was 0.52 and this was determined using the table of page on page 7.

The warm suspension was then filtered through a preheated filter (65° C.). The filter cake was washed twice with rinsings (EtOH/H$_2$O, 13 g/2 g) from the reactor. The resulting yellow solid was dried in a vacuum oven at 100 mbar, 40° C. for 8-12 hours to yield 13.5 g (70%) of a crystalline yellow solid (>98% pure; >98% single polymorph. The product matched the analytical profile of Form B described in Example 10 of WO2006/127926 including XRPD and FTIR (see below).

Example 2

Preparation of the Crystalline Anhydrous Form of 4-amino-5-fluoro-3-[6-(4-methylpiperazin-1-yl)-1H-benzimidazol-2-yl]-1H-quinolin-2-One Lactic Acid Salt (Anhydrous Form II)

A 500 ml double jacket reactor with a condenser, temperature probe, nitrogen inlet, and mechanical stirrer was purged with nitrogen. The reactor was charged with 15.0 g 4-amino-5-fluoro-3-[6-(4-methylpiperazin-1-yl)-1H-benzimidazol-2-yl]-1H-quinolin-2-one as the free base, 8.3 g concentrated D,L-lactic acid (containing 85% lactic acid, and 15% water), 160 g water-free toluene. The mixture was stirred vigorously (100 rpm) to form a brownish suspension and heated to an external temperature of 60° C. over 1 h (internal temperature of 58° C.). Seed of crystals of form II can be prepared according to WO2009/115562. Seed crystals of Form II (0.12 g) were added to the suspension immediately upon reaching 60° C. The suspension was stirred at this temperature for 4 h. The water activity in the present example is close to 0, the water activity is of about 0.06 and was calculated according to the table page 7 and the water fraction, including the water contained in the D,L lactic acid concentrate, of the reactor.

The warm suspension was then filtered through a filter. The filter cake was washed twice with the ethanol used to rinse the reactor. The resulting yellow solid was dried in a vacuum oven at 100 mbar, 40° C. for 8-12 hours to yield 14.5 g (74%) of a crystalline yellow solid (>98% pure; >98% single polymorph. The product matched the analytical profile of anhydrous Form II described in WO2009/115562, see FIG. 1.

Example 3

Preparation of Crystalline Anhydrous Form 4-amino-5-fluoro-3-[6-(4-methylpiperazin-1-yl)-1H-benzimidazol-2-yl]-1H-quinolin-2-One Lactic Acid Salt (Anhydrous Form II)

A suspension of 30.0 g 4-amino-5-fluoro-3-[6-(4-methylpiperazin-1-yl)-1H-benzimidazol-2-yl]-1H-quinolin-2-one lactic acid salt prepared as referred to in Example 1 above and 1.0 g of 85 wt % lactic acid in absolute ethanol (200 g) was heated to 60° C. The stirring was continued at 60° C. for 20 h at 200 rpm stirrer speed. The warm suspension was filtered, and the crystals were dried for 8 h at 40° C. under vacuum (100 mbar). Yield: 28 g yellowish powder (93%). The product matched the analytical profile of Form II described in WO2009/115562 including XRPD, see FIG. 1 of WO2009/115562.

Example 4

Preparation of Crystalline Monohydrate Form 4-amino-5-fluoro-3-[6-(4-methylpiperazin-1-yl)-1H-benzimidazol-2-yl]-1H-quinolin-2-One Lactic Acid Salt (Form B)

A suspension of 5.0 g 4-amino-5-fluoro-3-[6-(4-methylpiperazin-1-yl)-1H-benzimidazol-2-yl]-1H-quinolin-2-one lactic acid salt prepared as in Example 1 above and 3.0 g of depolymerised lactic acid in absolute ethanol (27 g) and water (3 g) was heated to 65° C. The stirring was continued at 65° C. for 20 h at 150 rpm stirrer speed. The water activity in the present example is of about 0.56 and was calculated as described in the former examples. The warm suspension was filtered, at 60° C. and the crystals were dried for 8 h at 40° C. under vacuum (100 mbar). Yield: 4.15 g yellowish powder (83%). The product matched the analytical profile of the monohydrate Form B described in Example 10 of WO2006/127926 including XRPD, see FIG. 6 of WO WO2006/127926.

Example 5

Preparation of the Crystalline Monohydrate Form of 4-amino-5-fluoro-3-[6-(4-methylpiperazin-1-yl)-1H-benzimidazol-2-yl]-1H-quinolin-2-One Lactic Acid Salt (Form B) from a Polymorph Mixture of Lactic Acid Salts A 500 ml double jacket reactor with a condenser, temperature probe, nitrogen inlet, and mechanical stirrer was purged with nitrogen. The reactor was charged with 30.0 g 4-amino-5-fluoro-3-[6-(4-methylpiperazin-1-yl)-1H-benzimidazol-2-yl]-1H-quinolin-2-one LACTIC ACID SALT (mixture of polymorphs or "undesired" polymorph), 3.0 g depolymerized D,L-lactic acid (containing 37% lactic acid, of which 92% was monomer, and 63% water; prepared from 85 wt % D,L-lactic acid that was stirred in 100° C. water for 20-24 h), 165 g water-free ethanol, and 14 g water. The mixture was stirred vigorously (100 rpm) to form a brownish suspension and heated to an external temperature of 60° C. over 1 h (internal temperature of 58° C.). Seed crystals of Form B (0.24 g) were added to the suspension immediately upon reaching 60° C. The suspension was stirred at this temperature for 8 h. The water activity in the present example is of about 0.41, calculated as in the former examples.

The warm suspension was then filtered through a preheated filter (65° C.). The filter cake was washed twice with rinsings (EtOH/H$_2$O, 13 g/2 g) from the reactor. The resulting yellow solid was dried in a vacuum oven at 100 mbar, 40° C. for 8-12 hours to yield 26.7 g (89%) of a crystalline yellow solid (>98% pure; >98% single polymorph. The product matched the analytical profile of Form B described in Example 10 and/or FIG. 6 of WO2006/127926 regarding XRPD and FTIR.

Example 6

X-Ray Powder Diffraction

X-ray powder diffraction analysis on the Form B (monohydrate) and Form II (anhydrous) polymorphs of 4-amino-5-fluoro-3-[6-(4-methylpiperazin-1-yl)-1H-benzimidazol-2-yl]-1H-quinolin-2-one lactic acid salt was carried out using CuKα radiation. The standard error for peak positions obtained in this technique is ±0.2° θ. The XRPD pattern for Form B matched that shown in FIG. 66 of WO 2006/127926, and the relatively prominent two-theta peaks are presented in Table 1. The XRPD pattern for Form II matched that shown in FIG. 1 of WO 2009/115562, and the relatively prominent two-theta peaks are presented in Table 2. The fact that the angle 2-theta values of the below table and the ones of Example 10 of WO2006/127926 can exhibit a difference of 0.1 or 0.2 is understood by the person skilled in the art as being within the acceptable variation of the performed measures.

TABLE 1

List of Most Significant Peaks of Form B

| Angle (2-Theta °) | Relative Intensity |
|---|---|
| 7.6 | Low |
| 11.8 | Medium |
| 12.8 | Medium |
| 15.3 | Medium |
| 16.1 | Medium |
| 17.5 | High |
| 18.4 | Medium |
| 19.24 | High |
| 23.2 | High |
| 23.4 | High |
| 25.9 | High |
| 28.0 | High |
| 29.2 | High |
| 29.8 | Medium |

TABLE 2

List of Most Significant Peaks of Form II

| Angle (2-Theta °) | Relative Intensity |
|---|---|
| 11.8 | Medium |
| 12.9 | Medium |
| 13.8 | Medium |
| 14.7 | Medium |
| 16.7 | Medium |
| 18.5 | High |
| 19.8 | Medium |
| 20.4 | Medium |
| 20.9 | Medium |
| 21.8 | Medium |
| 23.8 | Medium |
| 25.3 | Medium |
| 25.6 | High |
| 26.9 | Medium |
| 28.0 | Medium |
| 29.2 | Medium |

Example 7

FTIR

Figure 2:
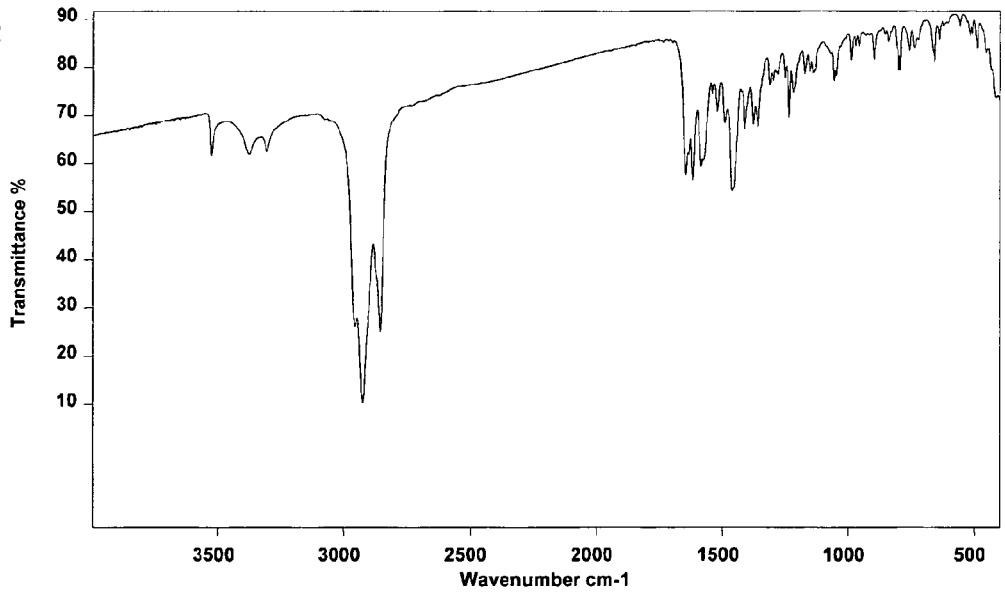
FIG. 2 shows an illustrative embodiment of the FTIR spectrum of the Form II polymorph of anhydrous 4-amino-5-fluoro-3-[6-(4-methylpiperazin-1-yl)-1H-benzimidazol-2-yl]-1H-quinolin-2-one lactic acid salt.

FT-IR analysis on the Form B (monohydrate) and Form II (anhydrous) polymorphs of 4-amino-5-fluoro-3-[6-(4-methylpiperazin-1-yl)-1H-benzimidazol-2-yl]-1H-quinolin-2-one lactic acid salt was carried out in nujol between 2 KBr plates. The standard error for peak positions obtained in this technique is ±2 cm$^{-1}$. FIG. 1 shows a representative FT-IR spectrum for Form B and FIG. 2 shows a representative FT-IR spectrum for Form II. Table 3 lists characteristic absorption bands for each polymorph.

TABLE 3

| Form | Characteristic Absorption Bands (cm$^{-1}$) |
|---|---|
| Form B | 3526, 3380, 2925, 2854, 1636, 1618, 1589, 1571, 1540, 1524, 1496, 1464, 1412, 1362, 1278, 1255, 1238, 1223, 1170, 1139, 1119, 1059, 991, 970, 895, 798, 759, 665, 643, 559, 516, 487, 421 |
| Form II | 3524, 3376, 3305, 2924, 2854, 1644, 1617, 1585, 1520, 1464, 1411, 1360, 1313, 1235, 1218, 1174, 1056, 989, 957, 899, 802, 796, 760, 660, 558, 489 |

As will be understood by one skilled in the art, for any and all purposes, particularly in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

While certain embodiments have been illustrated and described, it should be understood that changes and modifications can be made therein in accordance with ordinary skill in the art without departing from the present technology in its broader aspects as defined in the following claims.

What is claimed is:

1. A method of making Form B, a monohydrate crystalline form of a lactic acid salt of a compound of formula I,

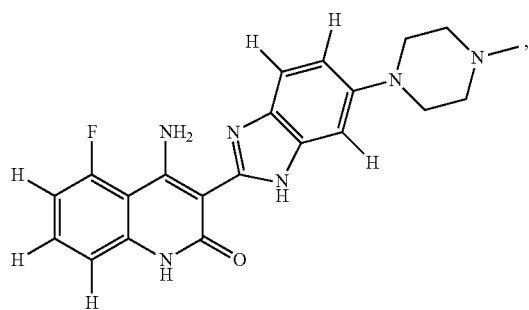

comprising:
heating to a temperature ranging from 50 to 70° C. a suspension of the free base of the compound of formula I or a polymorphic form or a mixture of polymorphs of the lactic acid salt of compound of formula I and lactic acid in a solution comprising at least two solvents and a water activity of about 0.3 to about 0.6;
and,
isolating crystals of at least 90% pure form B from the solution at a temperature ranging from 50 to 60° C., wherein the CuKα XRPD pattern for the Form B has 2Θ peaks at 7.6°, 11.8°, 12.8°, 15.3°, 16.1°, 17.5°, 18.4°, 19.24°, 23.2°, 23.4°, 25.9°, 28.0°, 29.2° and 29.8°±0.2°, respectively.

2. The method of claim 1 wherein the lactic acid is D,L-lactic acid.

3. The method of claim 1 wherein the lactic acid is depolymerized lactic acid.

4. The method of claim 1 wherein the suspension comprises about 1 to about 3 molar equivalents of lactic acid per molar equivalent of the compound of formula I.

5. The method according to claim 1 wherein the solution comprises one or more $C_{1-4}$ alcohol.

6. The method according to claim 5 wherein the $C_{1-4}$ alcohol is selected from methanol, ethanol, n-propanol, isopropanol, n-butanol, sec-butanol, isobutanol, tert-butanol, or a mixture of any two or more thereof.

7. The method according to claim 6 wherein the alcohol is absolute ethanol.

8. The method according to claim 1 wherein the solution contains about of about 8 wt % to about 16 wt % water in ethanol.

9. The method according to claim 8 wherein the solution contains about 12 wt % to about 14 wt % water in ethanol.

10. The method according to claim 1 wherein the isolation of the crystals is performed at a temperature of about 50° C. to about 60° C.

11. The method according to claim 1 further comprising drying the isolated crystals of Form B under reduced pressure.

12. The method according to claim 11, wherein the crystals are dried at a temperature in the range of about 30° C. to about 60° C.

13. The method of claim 1 wherein
the suspension comprises about 1.5 to about 2.5 molar equivalents of depolymerized D,L-lactic acid per molar equivalent of the compound of formula I;
the solution contains about 12 wt % to about 14 wt % water in ethanol;
the suspension is heated to a temperature ranging from at least about 60° C. to about 70° C.; and
the crystals of at least 90% Form B are isolated from the solution at a temperature of at least about 60° C.

14. The method of claim 1 wherein the isolated crystals comprises at least 95 wt % Form B.

* * * * *